(12) United States Patent
DelHoyo et al.

(10) Patent No.: US 7,010,108 B2
(45) Date of Patent: Mar. 7, 2006

(54) METHOD FOR SCHEDULING VIDEOCONFERENCES

(75) Inventors: Sergio Jason DelHoyo, Leesburg, VA (US); Robert Scott Kaplan, Burke, VA (US); Xiaoping Xu, Herndon, VA (US)

(73) Assignee: Magicsoft Corporation, Reston, VA (US)

( * ) Notice: Subject to any disclaimer, the term of this patent is extended or adjusted under 35 U.S.C. 154(b) by 68 days.

(21) Appl. No.: 10/371,308

(22) Filed: Feb. 21, 2003

(65) Prior Publication Data

US 2004/0165710 A1    Aug. 26, 2004

(51) Int. Cl.
*H04M 3/42* (2006.01)
*H04N 5/225* (2006.01)
*H04L 12/28* (2006.01)

(52) U.S. Cl. .............................. 379/202.01; 348/219.1; 370/256; 370/260

(58) Field of Classification Search ........... 379/202.01; 370/256, 260; 348/219, 219.1, 218.1
See application file for complete search history.

(56) References Cited

U.S. PATENT DOCUMENTS

| 5,408,526 | A | * | 4/1995 | McFarland et al. ..... 379/202.01 |
| 5,541,639 | A | | 7/1996 | Takatsuki et al. ............. 348/15 |
| 5,631,904 | A | | 5/1997 | Fitser et al. ................ 370/261 |
| 5,999,525 | A | | 12/1999 | Krishnaswamy et al. ... 370/352 |
| 6,064,976 | A | | 5/2000 | Tolopka ........................ 705/9 |
| 6,167,432 | A | | 12/2000 | Jiang .......................... 709/204 |
| 6,295,350 | B1 | | 9/2001 | Schreyer et al. ............ 379/221 |
| 6,353,596 | B1 | * | 3/2002 | Grossglauser et al. ...... 370/256 |
| 6,418,398 | B1 | | 7/2002 | Dueck et al. ................ 702/181 |
| 6,671,262 | B1 | * | 12/2003 | Kung et al. ................. 370/260 |
| 2003/0028535 | A1 | | 2/2003 | Sheldon et al. .............. 707/10 |
| 2003/0028656 | A1 | | 2/2003 | Babka ........................ 709/229 |

OTHER PUBLICATIONS

"Algorithms in C++", treatise by Robert Sedgewick, pp. 476-478, Princeton University, 1992.

\* cited by examiner

*Primary Examiner*—Ahmad F. Matar
*Assistant Examiner*—Thjuan P. Knowlin
(74) *Attorney, Agent, or Firm*—Roberts, Mlotkowski & Hobbes

(57) ABSTRACT

A method for connecting a videoconference through a telecommunication system including multiple telecommunication devices and endpoint stations operatively connected via route segments.

3 Claims, 4 Drawing Sheets

METHOD FOR SCHEDULING VIDEOCONFERENCES

This invention relates to the field of telecommunications and videoconferencing. In particular, it relates to methods and software for scheduling telecommunication conferencing having audio and video presentation.

BACKGROUND OF THE INVENTION

Modern communications has evolved a wide variety of devices and technologies, used for linking both public and private telecommunication networks capable of communicating between various endpoint stations, such as videoconferencing (VC) rooms and desktop computers, for real-time visual communication and collaboration. Since the endpoint stations may be located in diverse places and served by a variety of different networks and telecom devices, linking these endpoints in a single real-time multimedia conferencing event can be very complex, especially in geographically dispersed commercial, educational, or governmental facilities.

Videoconferencing is a form of real-time communication across long distances with video and audio contact that may also include graphics and data exchange. Digital video transmission systems typically comprise camera, codec (coder-decoder), network access equipment, network facilities, and audio components. Various technologies established by the International Telecommunication Union standards-setting body ("ITU-T") may be used in constructing a videoconference over ISDN (H.320), IP (H.323), and ATM (H.321) networks. The communications equipment and channels linking the multiple VC rooms are operatively connected through these telecom modules and/or networks. The physical links may include conventional telephone lines, wireless transmitters, fiber optic systems, satellites, etc. Within the network, VC technology uses several commercially available telecom devices to bridge and switch together multiple endpoints into a single videoconference. A Multipoint Control Unit (MCU) is such a device that allows more than three individual videoconference endpoint units to connect together to form a multiparty videoconference session. The MCU device uses fast switching techniques to patch the presenter's or speaker's input to the output ports representing the other participants. A router or switch is a device that connects segments of the network together to allow a continuous path for the video stream to reach all participant endpoints in the videoconference.

Because of the variety of networks and subsystems encountered in videoconferencing, the differences in standards and protocols, and the limited resource capacity of network devices and segment routes; the complexity of creating a successful videoconference using the most efficient routing through human management usually results in a low order of success. An Automated Scheduling System using specialized algorithms and modeling techniques allows for a computer system to accurately schedule and route videoconferences with the highest order of success.

SUMMARY OF THE INVENTION

The present invention provides a computer-implemented technique for scheduling and conducting videoconferencing in a complex telecommunications environment by providing a novel method for connecting a videoconference through a telecommunication system comprising a plurality of telecommunication devices and a plurality of endpoint stations.

The system provides a database in a telecommunication Operations Center facility including at least an initial configuration for a network model of the telecommunication system. The initial scheduling steps involve entering endpoint indicia (e.g.—H323 alias, IP address, dial string, User ID, bandwidth, etc.), and telecommunications device operating indicia into the database. Information is also entered about the operating and cost parameters of the route segments (often called pipes) between the endpoint and telecom devices.

Automatic allocation of telecom routing is affected by establishing an adjacency matrix with nodes based on route segments between each operatively connected endpoint station and telecommunication device; assigning efficiency values to each route segment in the matrix; and calculating the most efficient routing for the videoconference by employing an allocation graph algorithm. This novel process can provide for nominating a primary telecom device for interconnecting the system via selected route segments. Nominating a primary device is followed by verifying operability of the network model of the telecommunication system through conference event counting for capacity allocation and automatic conference call launching through an automated device control system. With the successful scheduling and route allocation steps recorded into the database at the Operations Center facility, the VC event can be initiated automatically over reserved facilities at the elected time.

DETAILED DESCRIPTION

EXAMPLE 1

Automated Scheduling and Least Cost Routing

Figure 1:
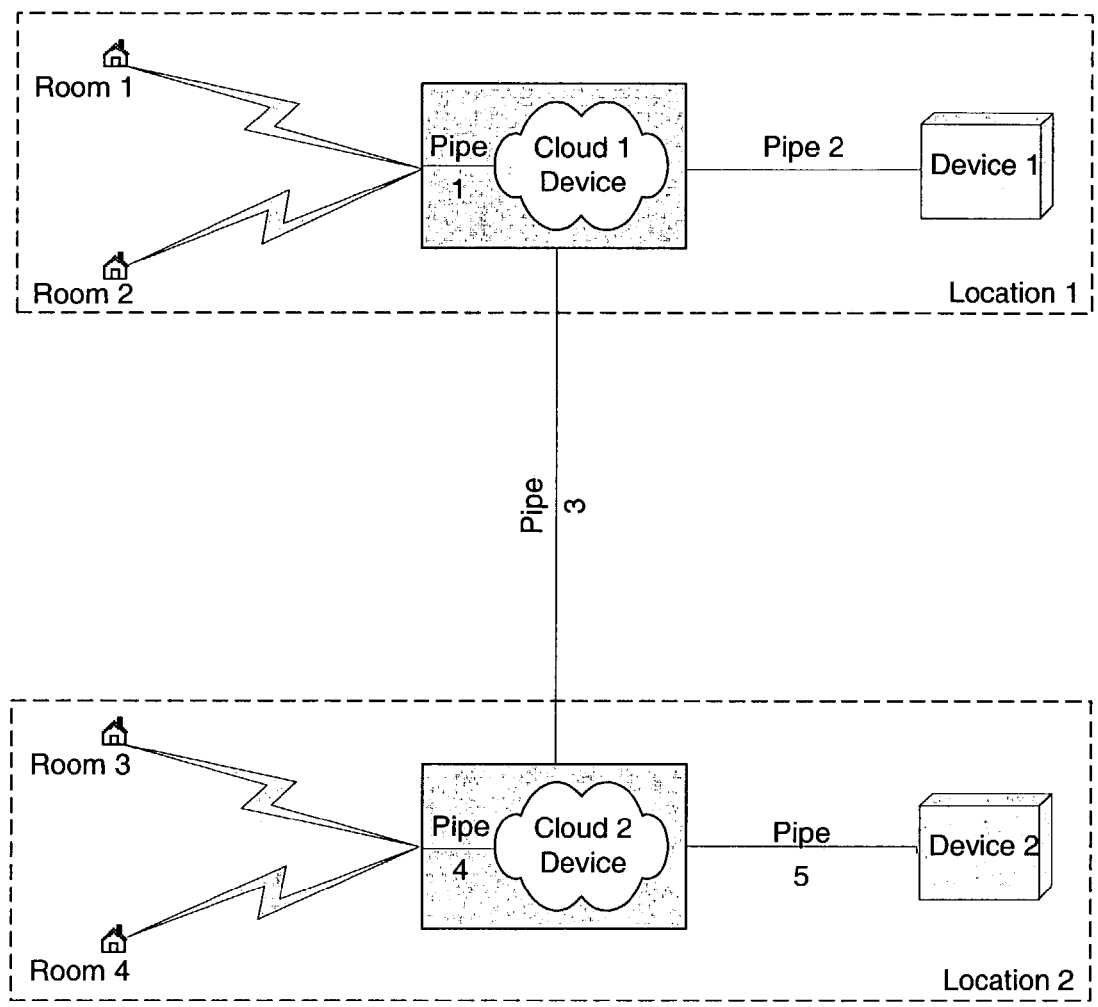
FIG. 1 is a schematic diagram depicting a telecommunications system for videoconferencing.

Example 1 demonstrates how a programmed computer with interactive software provides a preferred computational method for connecting a videoconference through a telecommunication system comprising multiple telecommunication devices and endpoint stations. The successive steps are:

1) providing a database in a telecommunication host facility including an initial configuration of a network model for the telecommunication system;
2) entering endpoint-operating indicia (e.g.—address, equipment specs, etc.) at the host facility database;
3) entering telecommunications device operating indicia (e.g.—MCU identification, bandwidth, etc.) at the host facility database;
4) establishing an adjacency matrix based on route segments between each operatively connected endpoint station and telecommunication device;

5) optionally assigning efficiency values to each route segment (hop) in the matrix, provided there exists unequal value;
6) automatically calculating the most efficient routing for the videoconference by employing a Floyd-type graph algorithm;
7) nominating a primary device for interconnecting the system;
8) verifying operability of a network model of the telecommunication system; and
9) recording verified routing in the host facility database.

Example 1 uses VC Wizard™ software (supplied by Magicsoft Corp., Chantilly, Va., USA).

When the VC System schedules a videoconference, the program poses and answers several questions, including:
Are the desired rooms and persons available?
Are the desired rooms compatible?
What device can host this conference?
What is the best way to connect rooms to the host device?
Example 1 explains the algorithm the VC System uses to answer these questions. The result is a successfully scheduled videoconference using the most efficient routes between endpoints and devices.

Terminology

Several terms have specialized meanings in the context of Example 1. Refer to Table 1 for definitions of these terms. Related terms are grouped together for comparison.

TABLE 1

Terminology

| Term | Definition |
| --- | --- |
| Device | Logical construct in the network model that is not an endpoint and handles videoconferencing traffic, such as a switch, network cloud, or bridge. |
| Bridge | Subcategory of devices. A device that combines multiple inputs so that three or more parties can participate in a videoconference. Also called an MCU. |
| MCU | Multipoint Control Unit. Subcategory of devices. A device that combines multiple inputs so that three or more parties can participate in a videoconference. |
| Switch | Subcategory of devices capable of routing traffic and hosting a limited variety of conferences. |
| Pipe | Connection between two rooms or devices. Pipes have types, such as ISDN and IP. |
| Endpoint | The combination of hardware and software required to view and participate in a videoconference. The endpoint handles encoding, decoding, and communications with the bridge and other endpoints. |
| Room | Logical construct in the network model that represents an endpoint. |
| Person | In the VC system, someone associated with a videoconference, either as a participant or technical contact. |
| Resource | A person, room, or device requested for a videoconference. |
| VC System | Videoconferencing System (i.e.- VC Wizard) |

Prerequisites

To execute the allocation algorithm, the system data supplied includes specific information about the conference, which the user enters at the time of scheduling; and details about the videoconferencing network, which is configured as a network model when the VC System is installed.

Data Entered at Time of Scheduling

A typical VC system requires the following minimum information:

TABLE 2

User-supplied data required for the allocation algorithm.

| Field | Data Source |
| --- | --- |
| Conference ID | Automatically assigned by the VC System. Used as a unique identifier to tag and retrieve information associated with this conference. |
| Start Date | Required field. Entered by user. |
| Start Time | Required field. Entered by user. |
| Duration | Required field. Entered by user in days, hours, and minutes. |
| Reservation Type | Required field. Selected by user. |
| Persons in Conference | Entered by user. A person can be a participant or technical support contact. |
| Room In Conference | Entered by user. A room is equivalent to a video endpoint. |
| Primary Device | Only if user selects a device. By default, this field is blank and is populated at the end of the algorithm. |

Based on this information, the program determines and allocates the most efficient route between the endpoints and devices involved in the videoconference.

The Network Model

When the VC System is first installed, a user configures the network model. This model is a virtual representation of the user's real-world videoconferencing network and includes:
all endpoints and devices in the network
capacity limitations for all devices
all connections, or pipes, in the network
types and capabilities for all pipes FIG. 1 shows the network model used in Example 1. A significant portion (steps 5 and 6 below) of the algorithm focuses on rendering this model in a way that allows the program to determine how endpoints and devices connect.

The network comprises two separate videoconferencing hubs, Location 1 and Location 2. Each room is a videoconferencing endpoint. In this model, all rooms link to the network with dial-up connections to network cloud devices. Devices 1 and 2 represent MCUs connected to the network by ISDN or Internet. The cloud devices also connect to each other by a public switched ISDN network or the Internet.

When a videoconference includes rooms from both locations, the VC System software determines the most efficient way to host the conference based on least-cost routing. This kind of routing becomes very important when linking videoconferencing networks in different parts of the country or around the world.

For example, assume Rooms 1, 2, and 3 participate in a conference. In this case, it is much more efficient to host the conference on Device 1 than on Device 2. Hosting on Device 1 requires traffic from one room to travel across Pipe 3 to the other location, but hosting on Device 2 requires traffic from two rooms to travel across Pipe 3 to the other location.

Process Overview

This section provides an overview of the steps required to determine and allocate the most efficient route between endpoints:
1. Retrieve information from the VC System database.
2. Check resource availability.
3. Check room compatibility.
4. Check all devices as:
candidates for bridging device
candidates for switching device 5. Generate an adjacency matrix with nodes representing telecom devices and endpoints.
6. Determine the most efficient route between all endpoints and devices.
7. Nominate a bridging device.
8. Generate the actual route from each endpoint to the bridging device.
9. Allocate the actual route from each endpoint to the bridging device.
10. Store allocated resources in the database.

Figure 2:
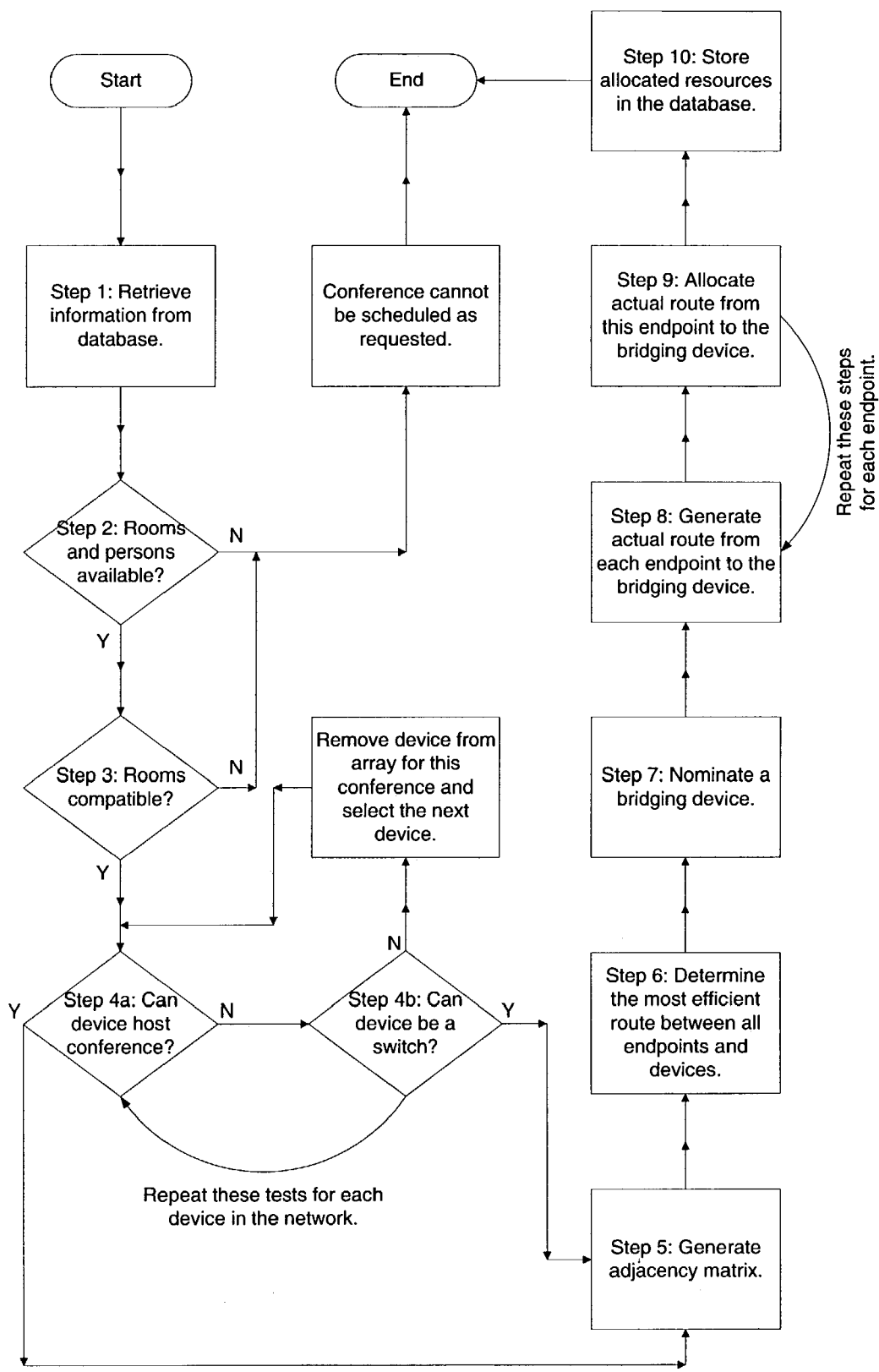
FIG. 2 is flow chart illustrating an allocation algorithm according to the present invention.

FIG. 2 represents these steps graphically as a flowchart.

How Reservation Type Affects the Algorithm

The type of reservation the user selects determines which of these steps are executed. Table 3 shows the relationship between reservation type and the algorithm's execution.

TABLE 3

Steps executed for each reservation type.

| Reservation Type | Steps Executed | Factors Checked in These Steps |
| --- | --- | --- |
| Room Reservation | 1–2, 10 | Resource availability for date and time |
| Room Compatibility | 1–3, 10 | Resource availability for date and time<br>Compatibility of video parameters |
| Network Reservation | 1–10 | Resource availability for date and time |
| Network Control | | Compatibility of video parameters<br>Availability of network resources (channels, bandwidth, etc.) |

For the purposes of this algorithm, the program treats Network Reservation and Network Control the same. The difference between these reservation types becomes important only when VC Wizard launches the conference automatically.

Step 1: Retrieve Information from the Database

Based on the conference ID (see Table 2), the program generates the following single-dimension arrays:

TABLE 4

Arrays generated at beginning of algorithm execution.

| Array Name | Information in Array |
| --- | --- |
| Sites | Properties of all rooms included in the conference, including each room's hub connections. |
| Persons | Properties of all persons included in the conference. |

The program generates these arrays to perform steps 2–10.

Step 2: Check Resource Availability

The program determines whether each room and person included in the conference is available at the specified date and time, based on the Sites and Persons arrays in Table 4. Availability is constrained by:

time of day
   The user may specify times of day when a room or person cannot be scheduled for a conference. For example, a person may not be available before 7:00 A.M.
day of week
   The user may specify days of the week when a room or person cannot be scheduled for a conference. For example, a person may not be available on Saturdays and Sundays.
holidays
   The user may specify holidays when a room or person cannot be scheduled for a conference. For example, the room may not be available on federal holidays.
other conferences
   A room or person is considered available only if not scheduled for another conference at the same date and time.

If all selected rooms and persons are available at the desired date and time, the conference passes to step:
   10, if the conference is a Room Reservation,
   3, if the conference is Room Compatibility, Network Reservation, or Network Control Otherwise, the system returns an error informing the user that one or more rooms or persons are not available at the requested date and time.

Step 3: Check Room Compatibility

The program determines whether each room included in the conference is compatible with the conference parameters, based on the Sites array in Table 4. The room compatibility check is based on the capabilities shown in Table 5.

TABLE 5

Capabilities included in room compatibility check.

| Capability | Description |
| --- | --- |
| Speed | Transmission speed, in kilobytes per second. |
| Audio Format | Audio encoding standards. |
| Video Format | Video encoding standards. |
| Frame Rate | Transmission speed, in frames per second. |
| Protocol | Videoconferencing standards and protocols. |
| User-defined capabilities | A custom field used to match rooms with similar characteristics.<br>Example: A user-defined capability called "Clearance Level" with possible values of classified, secret, and top secret. |

If all selected rooms are compatible with the conference parameters for each of these capabilities, the conference passes to step:
   10 if the conference is Room Compatibility
   4 if the conference is Network Reservation or Network Control.

Otherwise, the system returns an error informing the user that one or more capabilities are not compatible for the selected rooms.

Step 4: Check all Devices as Bridges or Switches

The program generates a single-dimension array of devices. This array contains all devices in the network model. If the conference has already been scheduled and the user is editing it, then the Device array contains additional information for those devices currently allocated in the conference.

Then, the program checks each device as a potential bridge or switch for this conference.

For the purposes of illustration, assume that the conference must include Rooms 1, 2, and 3. The user has not selected a primary device, so the program must test each device in the network as a bridge or switch.

Check MCU (Bridge) Device Compatibility

Bridge device compatibility includes tests for device compatibility with the conference parameters and resource availability on the device.

Compatibility with Conference Parameters

A bridging device:

is compatible with the conference parameters can potentially host the conference acts as a terminus and does not pass traffic on to another device has sufficient capacity to host the conference The program tests each device in the array as a potential bridging device. Based on information in the device driver, the program determines whether each device meets the criteria for the conference parameters.

Device Availability as Determined by Resource Counting

Figure 3:
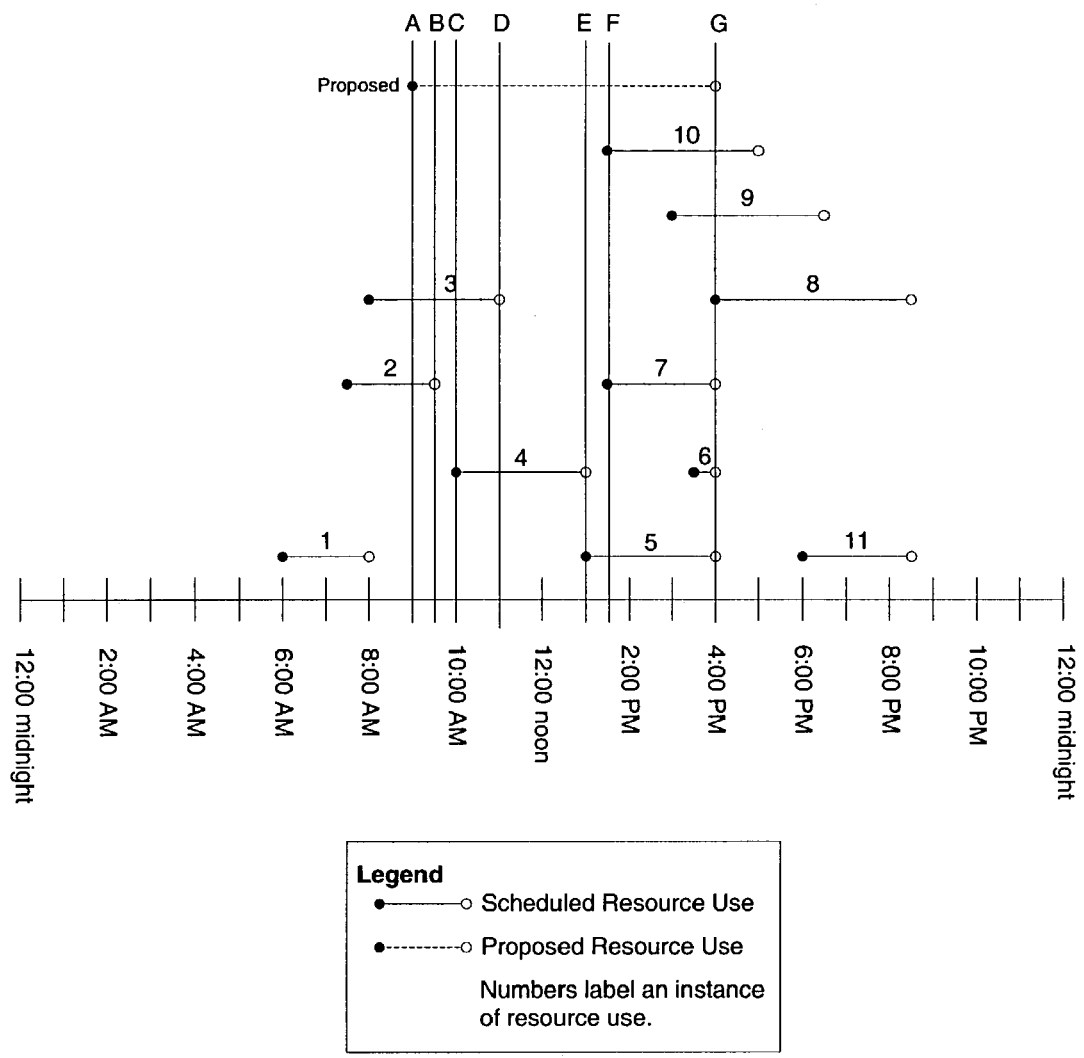
FIG. 3 is a diagram depicting the resource counting algorithm.

On those devices that match the conference parameters, the software performs a further test to confirm device availability. This test prevents a device from being scheduled beyond its capacity at any given time. Refer to FIG. 3, which illustrates resource counting.

FIG. 3 shows that 11 conferences are already scheduled on the selected device on the proposed date. The software uses the resource counting algorithm to determine if the device's capacity allows the proposed conference to be scheduled, following these steps:

1. Determine the first conference that overlaps the proposed conference's time. In FIG. 3, the first conference that overlaps the proposed conference's time is Conference 2.
2. Create a new time period that is the intersection of the overlapping conference's time and the proposed conference's time. Lines A and B mark this intersection.
3. Generate a new list of conferences by including the remaining resources in use at anytime in the intersection time period. In FIG. 3, this list includes Conferences 2 and 3.

The size of this new list indicates the potential number of resources in use at the exact same time as the first resource in the original list. If the new list has only one resource in it, then that number is one. The software continues to step 4.

If the new list has more than one resource, then the software must recursively repeat steps 1–3 using the new time period and new list in place of the originals until a list size of one is reached. After reaching a list size of one, the software counts up the number of recursive calls to determine the number of resources in use at the exact same time.
4. Move on to each of the other resources in the list generating new time periods and new lists. For each resource, keep track of the number of other resources simultaneously in use and save the maximum number of recursive calls as the solution.
5. At anytime, if the number of remaining resources in a list is less than the current maximum number of recursive calls (determined in step 4), stop processing the current list and go back to the previous list of resources if there is one.

Checking the current list size against the current maximum count speeds up the calculation by omitting needless computation.
6. Confirm that the maximum count of resources in simultaneous use is less than the device's capacity limits. In FIG. 3, the maximum count is five. If the device can handle at least 6 conferences, then the proposed conference can be scheduled. Otherwise, this device cannot be used to host the proposed conference.

Results of Testing Devices as Possible Bridges

Those devices that pass both tests (compatibility and availability) are added to a bridge array. Those that fail are tested as switching devices. If no device meets the criteria for a bridge, the program returns an error to the user indicating that the conference cannot be scheduled as requested.

Based on the sample network represented in FIG. 1, assume that the conference must include Rooms 1, 2, and 3. In this case, the following devices meet the criteria for bridging devices:

Device 1

Device 2

Check Switching Device Compatibility

Switching device compatibility includes tests for device compatibility with the conference parameters and resource availability on the device.

Compatibility with Conference Parameters

A switching device:

is compatible with the conference parameters is not a terminus passes traffic on to another device or room has sufficient capacity to handle conference traffic The program tests each device that failed the bridge compatibility test as a switching device. Based on information in the allocation device driver, the program determines whether each device meets the criteria for the conference parameters.

Next, the program tests each device for available capacity using the algorithm described in the section "Device Availability as Determined by Resource Counting."

Those that pass both tests (compatibility and availability) are added to a switch array. Those that fail are excluded from this conference.

Based on the sample network represented in FIG. 1, assume that the conference must include Rooms 1, 2, and 3. In this case, Cloud 1 and Cloud 2 meet the criteria for switching devices.

Step 5: Generate an Adjacency Matrix

As a result of steps 1–4, the program has arrays of rooms, bridges, and switches for a particular conference, but no idea of how these are connected. To derive the most efficient route linking the rooms required for the conference, the program must first determine how they are connected.

Floyd's Algorithm

The classic shortest-path algorithm finds the shortest path form the start device to each of the other devices, using a method generally attributed to R. W. Floyd.

Computation is made for each route to determine if it is part of a new least costly path.

```
for (MiddleNode = 0; MiddleNode < TableSize; MiddleNode++)
  for (StartNode = 0; StartNode < TableSize; StartNode++)
    if (Table[StartNode][MiddleNode].LowestCost > 0)
      for (EndNode = 0; EndNode < TableSize; EndNode++)
        if (StartNode != EndNode &&
          Table[MiddleNode][EndNode].LowestCost > 0)
          {  NewCost = Table[StartNode][MiddleNode].LowestCost +
             Table[MiddleNode][EndNode].LowestCost;
             if (Table[StartNode][EndNode].LowestCost  ==0 ||
               Table[StartNode][EndNode].LowestCost > NewCost)
             {
               Table[StartNode][EndNode].LowestCost = NewCost;
               Table[StartNode][EndNode].From =
               Table[MiddleNode][EndNode].From;
             }
          }
```

How the Algorithm Determines Adjacency

To determine whether two endpoints or devices are adjacent, the program checks the Device and Site arrays for connections, or pipes, between each pair of starting and termination points in the network. If the starting and termination point have a common pipe name, then the program treats these points as adjacent. For example, Cloud 1 and Device 1 both include Pipe 2 in their lists of connections. Therefore, the program understands that these devices are adjacent. However, Room 1 and Device 2 do not include a common pipe name in their lists of connections, so these rooms are not adjacent.

The program creates an adjacency matrix to represent the connections in the network model. The matrix also stores the starting point for the most recent hop. At step 5, the starting point of the most recent hop is determined by simply referring to the row heading. However, as the algorithm continues, the starting point for the most recent hop cannot be determined from the matrix itself. Table 6 shows an adjacency matrix for the example conference including Rooms 1, 2, and 3. The matrix lists all rooms and devices that may be included in the conference. Rooms are always listed first in the matrix. A matrix entry of 0 corresponds to the absence of the indicated route.

TABLE 6

Adjacency matrix.

|    | R1    | R2    | R3    | D1    | C1    | D2    | C2    |
|----|-------|-------|-------|-------|-------|-------|-------|
| R1 |       | 0     | 0     | 0     | 1, R1 | 0     | 0     |
| R2 | 0     |       | 0     | 0     | 1, R2 | 0     | 0     |
| R3 | 0     | 0     |       | 0     | 0     | 0     | 1, R3 |
| D1 | 0     | 0     | 0     |       | 1, D1 | 0     | 0     |
| C1 | 1, C1 | 1, C1 | 0     | 1, C1 |       | 0     | 1, C1 |
| D2 | 0     | 0     | 0     | 0     | 0     |       | 1, D2 |
| C2 | 0     | 0     | 1, C2 | 0     | 1, C2 | 1, C2 |       |

The row headings are possible starting points for a connection. The column headings are possible termination points for a connection. Each cell contains the number of hops required to connect these points, followed by the starting point of the last hop in the connection.

Based on this matrix, the program knows that Room 1 is not connected to anything else except Cloud 1. This information limits the possible routes for a conference including Room 1.

On the other hand, Cloud 1 is attached to Rooms 1 and 2, Device 1, and Cloud 2. Therefore, Cloud 1 can provide intermediate connections between multiple rooms and devices.

Step 6: Determine the Most Efficient Route etween all Endpoints and Devices

In the network model in FIG. 1, each connection has a cost/efficiency value of 1. However, users can assign costs/efficiency values to connections when configuring the network model. When values greater than 1 are used, the cost of connecting endpoints increases. However, the principles used to calculate the cost remain the same.

Using the adjacency matrix in Table 6, the program determines the number of hops required to connect each non-adjacent endpoint and device. Based on this data, the program determines the cheapest route between each device and endpoint.

To determine the most efficient (i.e.—cheapest) route, the program applies Floyd's algorithm (ref: Robert Sedgewick, *Algorithms* in C++ (Reading, Mass.: Addison-Wesley Publishing Company, 1992), 476–478.) as follows:

Test each possible midpoint with every combination of start and endpoints.

Check that the start point and end point are not equal.

Check that the midpoint is not equal to the start point or endpoint in the test.

Confirm whether the current number of hops is more efficient than the number already in the matrix and:

replace the matrix's value with the current calculated value if the matrix value is 0 replace the matrix's value with the current calculated value if the matrix value is greater than the calculated value discard the calculated value if the matrix's value is less than the calculated value For example, Table 7 shows the processing for the combination of Room 1 as a midpoint and Room 2 as a starting point. The table confirms what the network model already illustrates: Room 1 is not "between" anything and cannot be used as a midpoint between two other rooms or devices.

TABLE 7

Testing most efficient route with R1 as midpoint and R2 as starting point.

| Start  | R2                                              | R2                                             | R2 | R2 | R2 | R2 | R2 |
|--------|-------------------------------------------------|------------------------------------------------|----|----|----|----|----|
| Middle | R1                                              | R1                                             | R1 | R1 | R1 | R1 | R1 |
| End    | R1                                              | R2                                             | R3 | D1 | C1 | D2 | C2 |
| Result | Invalid - middle cannot be equal to end | Invalid - start cannot be equal to end | 0  | 0  | 0  | 0  | 0  |

Table 8 shows how the matrix looks after the program has tested R1, R2, R3, D1, and C1 as possible midpoints. Values added as a result of these steps are shown in underlined text.

TABLE 8

Adjacency matrix after partial processing for number of hops.

|     | R1    | R2    | R3    | D1    | C1    | D2    | C2    |
|-----|-------|-------|-------|-------|-------|-------|-------|
| R1  |       | 2,C1  | 0     | 2,C1  | 1, R1 | 0     | 2,C1  |
| R2  | 2,C1  |       | 0     | 2,C1  | 1, R2 | 0     | 2,C1  |
| R3  | 0     | 0     |       | 0     | 0     | 0     | 1, R3 |
| D1  | 2,C1  | 2,C1  | 0     |       | 1, D1 | 0     | 2,C1  |
| C1  | 1, C1 | 1, C1 | 0     | 1, C1 |       | 0     | 1, C1 |
| D2  | 0     | 0     | 0     | 0     | 0     |       | 1, D2 |
| C2  | 2,C1  | 2,C1  | 1, C2 | 2,C1  | 1, C2 | 1, C2 |       |

The row headings are possible starting points for a connection. The column headings are possible termination points for a connection. Each cell contains the number of hops required to connect these points, followed by the starting point of the last hop in the connection.

For example, the cell at the intersection of D1 and R2 represents the connection between Device 1 and Room 2. The value in this cell indicates that this connection requires two hops, and the second hop begins at C1, or Cloud 1. Therefore, the program determines that Device 1 and Room 2 can be connected in two hops by way of Cloud 1.

Once the remaining possibilities have been tested (B2 and C2), the adjacency matrix (Table 9) shows the cost of connection between each pair of endpoints in the network.

TABLE 9

Adjacency matrix after applying Floyd's algorithm.

|    | R1    | R2    | R3    | D1    | C1    | D2    | C2    |
|----|-------|-------|-------|-------|-------|-------|-------|
| R1 |       | 2, C1 | 3, C2 | 2, C1 | 1, R1 | 3, C2 | 2, C1 |
| R2 | 2, C1 |       | 3, C2 | 2, C1 | 1, R2 | 3, C2 | 2, C1 |
| R3 | 3, C1 | 3, C1 |       | 3, C1 | 2, C2 | 2, C2 | 1, R3 |
| D1 | 2, C1 | 2, C1 | 3, C2 |       | 1, D1 | 3, C1 | 2, C1 |
| C1 | 1, C1 | 1, C1 | 2, C2 | 1, C1 |       | 2, C2 | 1, C1 |
| D2 | 3, C1 | 3, C1 | 2, C2 | 3, C1 | 2, C2 |       | 1, D2 |
| C2 | 2, C1 | 2, C1 | 1, C2 | 2, C1 | 1, C2 | 1, C2 |       |

Step 7: Nominate a Bridging Device

At this stage, the program has determined: 1) the cost/efficiency for connection between every possible room and device and 2) which devices can host the conference. Based on this combination of data, the program must select the device that can host the conference most efficiently.

Device 1 and Device 2 meet the criteria of a bridging device, so the program compares the costs of holding a conference hosted by each.

TABLE 10

Cost of hosting conference, by device.

| Rooms in   | Cost of Connection to |          |
|------------|-----------------------|----------|
| Conference | Device 1              | Device 2 |
| Room 1     | 2                     | 3        |
| Room 2     | 2                     | 3        |
| Room 3     | 3                     | 2        |
| Total Cost | 7                     | 8        |

The conference can be hosted more cheaply on Device 1, for a relative cost of 7, than on Device 2 for a cost of 8. Thus, the program nominates Device 1 as the primary device for this videoconference. If the cost of hosting the conference on each device is equal, the program chooses whichever device is first in the bridge array, which is the first device created in the network model. If the user specifies a primary device when creating the conference, the program skips step 7 and continues to step 8.

Step 8: Generate the Actual Route from each Endpoint to the Bridging Device

The algorithm performs steps 8 and 9 for each room in the conference, and then repeats these steps for all subsequent rooms. This sequence avoids allocating a connection or switch beyond its capacity.

After selecting Device 1 to host this conference, the program determines the actual route from each room to Device 1. The program begins with the following information:

R1 to D1 is 2, with C1 as the starting point of the last hop
R2 to D1 is 2, with C1 as the starting point of the last hop
R3 to D1 is 3, with C1 as the starting point of the last hop The integer indicates the number of hops between start and termination points. The ID indicates the start point of the most recent hop. Therefore, the program can determine these routes:

R1 to C1 to D1
R2 to C1 to D1

In both of these cases, there are only two hops, and the second hop begins with Cloud 1.

Determining Routes for Connections with Two or more Hops

Now the program must resolve the route from R3 to D1, based on a route with three hops and C1 as the starting point of the last hop.

R3 to x to C1 to D1, where x represents one or more intermediate points between R3 and C1

Based on the matrix in Table 9, the program can determine the route between R3 and C1, which is R3 to C2 to C1. Therefore, the missing intermediate point (x) in the route from R3 to D1 is C2, which yields this route for R3 to D1:

R3 to C2 to C1 to D1

Step 9: Allocate the Actual Routes from each Endpoint to the Bridging Device

Based on the route determined, the program allocates resources along the entire route to create a continuous path from the starting point to the ending point. For each hop in a route, the program reserves resources on the starting point, connection (pipe), and termination point.

Then, the program confirms that the entire connection meets all requirements for the conference (speed, bandwidth, etc.) and generates dial strings, if needed.

After executing confirmation steps for the first room, the program repeats them for each subsequent room.

In the example used above, the actual routes are:
R1 to C1 to D1
R2 to C1 to D1
R3 to C2 to C1 to D1 as shown on the network model. The diagram confirms that the program succeeded in allocating the most efficient route from each endpoint to the host device.

Because resources are reserved after each cycle, the program may reach a point where the most efficient route is unavailable. For example, the number of connections for a switch may be exceeded, causing the most efficient route to fail. In this case, the algorithm sets the value for this connection to 0 in the adjacency matrix (Table 9) and repeats steps 6 through 9 for this room and device pair.

Step 10: Store Allocated Resources in the Database

The algorithm saves information to the database to allocate the resources required for this conference. The type of resources reserved depends upon the reservation type the user selects (see Table 11).

TABLE 11

Information saved to database, by reservation type.

| Reservation Type    | Resources Reserved                                                                         |
|---------------------|--------------------------------------------------------------------------------------------|
| Room Reservation    | Rooms                                                                                      |
| Room Compatibility  | Persons                                                                                    |
| Network Reservation | Rooms                                                                                      |
| Network Control     | Persons                                                                                    |
|                     | Devices, including phone numbers and dial strings required to activate them                |
|                     | Ports                                                                                      |
|                     | Channels                                                                                   |

In addition, the algorithm changes the status of the conference to Scheduled. This status:

indicates that the persons, rooms, devices, ports, and channels associated with the conference are reserved for the conference's scheduled time prevents these resources from being booked for another conference during the same conference's scheduled time Adjacency Matrix Used in Example 1

This section shows how the algorithm uses Floyd's algorithm to calculate the most efficient routes between each endpoint and device.

The adjacency matrix resulting from step 6 is reproduced here for easy reference:

|    | R1    | R2    | R3    | D1    | C1    | D2    | C2    |
|----|-------|-------|-------|-------|-------|-------|-------|
| R1 |       | 0     | 0     | 0     | 1, R1 | 0     | 0     |
| R2 | 0     |       | 0     | 0     | 1, R2 | 0     | 0     |
| R3 | 0     | 0     |       | 0     | 0     | 0     | 1, R3 |
| D1 | 0     | 0     | 0     |       | 1, D1 | 0     | 0     |
| C1 | 1, C1 | 1, C1 | 1, C1 | 0     | 1, C1 | 0     | 1, C1 |
| D2 | 0     | 0     | 0     | 0     | 0     |       | 1, D2 |
| C2 | 0     | 0     | 1, C2 | 0     | 1, C2 | 1, C2 |       |

R1 Middle Point

| Start  | R1                                              | R1                                              | R1                                              | R1                                              | R1                                              | R1                                              | R1                                              |
|--------|-------------------------------------------------|-------------------------------------------------|-------------------------------------------------|-------------------------------------------------|-------------------------------------------------|-------------------------------------------------|-------------------------------------------------|
| Middle | R1                                              | R1                                              | R1                                              | R1                                              | R1                                              | R1                                              | R1                                              |
| End    | R1                                              | R2                                              | R3                                              | D1                                              | C1                                              | D2                                              | C2                                              |
| Result | Invalid - start cannot be equal to middle       | Invalid - start cannot be equal to middle       | Invalid - start cannot be equal to middle       | Invalid - start cannot be equal to middle       | Invalid - start cannot be equal to middle       | Invalid - start cannot be equal to middle       | Invalid - start cannot be equal to middle       |
| Start  | R2                                              | R2                                              | R2                                              | R2                                              | R2                                              | R2                                              | R2                                              |
| Middle | R1                                              | R1                                              | R1                                              | R1                                              | R1                                              | R1                                              | R1                                              |
| End    | R1                                              | R2                                              | R3                                              | D1                                              | C1                                              | D2                                              | C2                                              |
| Result | Invalid - middle cannot be equal to end         | Invalid - start cannot be equal to end          | 0                                               | 0                                               | 0                                               | 0                                               | 0                                               |
| Start  | R3                                              | R3                                              | R3                                              | R3                                              | R3                                              | R3                                              | R3                                              |
| Middle | R1                                              | R1                                              | R1                                              | R1                                              | R1                                              | R1                                              | R1                                              |
| End    | R1                                              | R2                                              | R3                                              | D1                                              | C1                                              | D2                                              | C2                                              |
| Result | Invalid - middle cannot be equal to end         | 0                                               | Invalid - start cannot be equal to end          | 0                                               | 0                                               | 0                                               | 0                                               |
| Start  | D1                                              | D1                                              | D1                                              | D1                                              | D1                                              | D1                                              | D1                                              |
| Middle | R1                                              | R1                                              | R1                                              | R1                                              | R1                                              | R1                                              | R1                                              |
| End    | R1                                              | R2                                              | R3                                              | D1                                              | C1                                              | D2                                              | C2                                              |
| Result | Invalid - middle cannot be equal to end         | 0                                               | 0                                               | Invalid - start cannot be equal to end          | 0                                               | 0                                               | 0                                               |
| Start  | C1                                              | C1                                              | C1                                              | C1                                              | C1                                              | C1                                              | C1                                              |
| Middle | R1                                              | R1                                              | R1                                              | R1                                              | R1                                              | R1                                              | R1                                              |
| End    | R1                                              | R2                                              | R3                                              | D1                                              | C1                                              | D2                                              | C2                                              |
| Result | Invalid - middle cannot be equal to end         | 0                                               | 0                                               | 0                                               | Invalid - start cannot be equal to end          | 0                                               | 0                                               |
| Start  | D2                                              | D2                                              | D2                                              | D2                                              | D2                                              | D2                                              | D2                                              |
| Middle | R1                                              | R1                                              | R1                                              | R1                                              | R1                                              | R1                                              | R1                                              |
| End    | R1                                              | R2                                              | R3                                              | D1                                              | C1                                              | D2                                              | C2                                              |
| Result | Invalid - middle cannot be equal to end         | 0                                               | 0                                               | 0                                               | 0                                               | Invalid - start cannot be equal to end          | 0                                               |
| Start  | C2                                              | C2                                              | C2                                              | C2                                              | C2                                              | C2                                              | C2                                              |
| Middle | R1                                              | R1                                              | R1                                              | R1                                              | R1                                              | R1                                              | R1                                              |
| End    | R1                                              | R2                                              | R3                                              | D1                                              | C1                                              | D2                                              | C2                                              |
| Result | Invalid - middle cannot be equal to end         | 0                                               | 0                                               | 0                                               | 0                                               | 0                                               | Invalid - start cannot be equal to end          |

At the end of this stage, the most efficient matrix looks like this:

|    | R1    | R2    | R3    | D1 | C1    | D2 | C2    |
|----|-------|-------|-------|----|-------|----|-------|
| R1 |       | 0     | 0     | 0  | 1, R1 | 0  | 0     |
| R2 | 0     |       | 0     | 0  | 1, R2 | 0  | 0     |
| R3 | 0     | 0     |       | 0  | 0     | 0  | 1, R3 |
| D1 | 0     | 0     | 0     |    | 1, D1 | 0  | 0     |
| C1 | 1, C1 | 1, C1 | 0     | 1, C1 |   | 0  | 1, C1 |

| | R1 | R2 | R3 | D1 | C1 | D2 | C2 |
|---|---|---|---|---|---|---|---|
| D2 | 0 | 0 | 0 | 0 | 0 | | 1, D2 |
| C2 | 0 | 0 | 1, C2 | 0 | 1, C2 | 1, C2 | |

There are no changes, showing that R1 does not make a good middle-point.

R2 Middle Point

| | | | | | | | |
|---|---|---|---|---|---|---|---|
| Start | R1 | R1 | R1 | R1 | R1 | R1 | R1 |
| Middle | R2 | R2 | R2 | R2 | R2 | R2 | R2 |
| End | R1 | R2 | R3 | D1 | C1 | D2 | C2 |
| Result | Invalid - start cannot be equal to end | Invalid - middle cannot be equal to end | 0 | 0 | 0 | 0 | 0 |
| Start | R2 | R2 | R2 | R2 | R2 | R2 | R2 |
| Middle | R2 | R2 | R2 | R2 | R2 | R2 | R2 |
| End | R1 | R2 | R3 | D1 | C1 | D2 | C2 |
| Result | Invalid - start cannot be equal to middle | Invalid - start cannot be equal to middle | Invalid - start cannot be equal to middle | Invalid - start cannot be equal to middle | Invalid - start cannot be equal to middle | Invalid - start cannot be equal to middle | Invalid - start cannot be equal to middle |
| Start | R3 | R3 | R3 | R3 | R3 | R3 | R3 |
| Middle | R2 | R2 | R2 | R2 | R2 | R2 | R2 |
| End | R1 | R2 | R3 | D1 | C1 | D2 | C2 |
| Result | 0 | Invalid - start cannot be equal to middle | Invalid - start cannot be equal to end | 0 | 0 | 0 | 0 |
| Start | D1 | D1 | D1 | D1 | D1 | D1 | D1 |
| Middle | R2 | R2 | R2 | R2 | R2 | R2 | R2 |
| End | R1 | R2 | R3 | D1 | C1 | D2 | C2 |
| Result | 0 | Invalid - middle cannot be equal to end | 0 | Invalid - start cannot be equal to end | 0 | 0 | 0 |
| Start | C1 | C1 | C1 | C1 | C1 | C1 | C1 |
| Middle | R2 | R2 | R2 | R2 | R2 | R2 | R2 |
| End | R1 | R2 | R3 | D1 | C1 | D2 | C2 |
| Result | 0 | Invalid - middle cannot be equal to end | 0 | 0 | Invalid - start cannot be equal to end | 0 | 0 |
| Start | D2 | D2 | D2 | D2 | D2 | D2 | D2 |
| Middle | R2 | R2 | R2 | R2 | R2 | R2 | R2 |
| End | R1 | R2 | R3 | D1 | C1 | D2 | C2 |
| Result | 0 | Invalid - middle cannot be equal to end | 0 | 0 | 0 | Invalid - start cannot be equal to end | 0 |
| Start | C2 | C2 | C2 | C2 | C2 | C2 | C2 |
| Middle | R2 | R2 | R2 | R2 | R2 | R2 | R2 |
| End | R1 | R2 | R3 | D1 | C1 | D2 | C2 |
| Result | 0 | Invalid - middle cannot be equal to end | 0 | 0 | 0 | 0 | Invalid - start cannot be equal to end |

At the end of this stage, the most efficient matrix looks like this:

|    | R1    | R2    | R3 | D1    | C1    | D2 | C2    |
|----|-------|-------|----|-------|-------|----|-------|
| R1 |       | 0     | 0  | 0     | 1, R1 | 0  | 0     |
| R2 | 0     |       | 0  | 0     | 1, R2 | 0  | 0     |
| R3 | 0     | 0     |    | 0     | 0     | 0  | 1, R3 |
| D1 | 0     | 0     | 0  |       | 1, D1 | 0  | 0     |
| C1 | 1, C1 | 1, C1 | 0  | 1, C1 |       | 0  | 1, C1 |

-continued

|    | R1 | R2 | R3    | D1 | C1    | D2    | C2    |
|----|----|----|-------|----|-------|-------|-------|
| D2 | 0  | 0  | 0     | 0  | 0     |       | 1, D2 |
| C2 | 0  | 0  | 1, C2 | 0  | 1, C2 | 1, C2 |       |

There are no changes, showing that R2 does not make a good middle-point.

R3 Middle Point

| Start | R1 | R1 | R1 | R1 | R1 | R1 | R1 |
|-------|----|----|----|----|----|----|----|
| Middle | R3 | R3 | R3 | R3 | R3 | R3 | R3 |
| End | R1 | R2 | R3 | D1 | C1 | D2 | C2 |
| Result | Invalid - start cannot be equal to end | 0 | Invalid - middle cannot be equal to end | 0 | 0 | 0 | 0 |
| Start | R2 | R2 | R2 | R2 | R2 | R2 | R2 |
| Middle | R3 | R3 | R3 | R3 | R3 | R3 | R3 |
| End | R1 | R2 | R3 | D1 | C1 | D2 | C2 |
| Result | 0 | Invalid - start cannot be equal to end | Invalid - middle cannot be equal to end | 0 | 0 | 0 | 0 |
| Start | R3 | R3 | R3 | R3 | R3 | R3 | R3 |
| Middle | R3 | R3 | R3 | R3 | R3 | R3 | R3 |
| End | R1 | R2 | R3 | D1 | C1 | D2 | C2 |
| Result | Invalid - start cannot be equal to middle | Invalid - start cannot be equal to middle | Invalid - start cannot be equal to middle | Invalid - start cannot be equal to middle | Invalid - start cannot be equal to middle | Invalid - start cannot be equal to middle | Invalid - start cannot be equal to middle |
| Start | D1 | D1 | D1 | D1 | D1 | D1 | D1 |
| Middle | R3 | R3 | R3 | R3 | R3 | R3 | R3 |
| End | R1 | R2 | R3 | D1 | C1 | D2 | C2 |
| Result | 0 | 0 | Invalid - middle cannot be equal to end | Invalid - start cannot be equal to end | 0 | 0 | 0 |
| Start | C1 | C1 | C1 | C1 | C1 | C1 | C1 |
| Middle | R3 | R3 | R3 | R3 | R3 | R3 | R3 |
| End | R1 | R2 | R3 | D1 | C1 | D2 | C2 |
| Result | 0 | 0 | Invalid - middle cannot be equal to end | 0 | Invalid - start cannot be equal to end | 0 | 0 |
| Start | D2 | D2 | D2 | D2 | D2 | D2 | D2 |
| Middle | R3 | R3 | R3 | R3 | R3 | R3 | R3 |
| End | R1 | R2 | R3 | D1 | C1 | D2 | C2 |
| Result | 0 | 0 | Invalid - middle cannot be equal to end | 0 | 0 | Invalid - start cannot be equal to end | 0 |
| Start | C2 | C2 | C2 | C2 | C2 | C2 | C2 |
| Middle | R3 | R3 | R3 | R3 | R3 | R3 | R3 |
| End | R1 | R2 | R3 | D1 | C1 | D2 | C2 |
| Result | 0 | 0 | Invalid - middle cannot be equal to end | 0 | 0 | 0 | Invalid - start cannot be equal to end |

At the end of this stage, the most efficient matrix looks like this:

|    | R1    | R2    | R3    | D1    | C1    | D2 | C2    |
|----|-------|-------|-------|-------|-------|----|-------|
| R1 |       | 0     | 0     | 0     | 1, R1 | 0  | 0     |
| R2 | 0     |       | 0     | 0     | 1, R2 | 0  | 0     |
| R3 | 0     | 0     |       | 0     | 0     | 0  | 1, R3 |
| D1 | 0     | 0     | 0     |       | 1, D1 | 0  | 0     |
| C1 | 1, C1 | 1, C1 | 0     | 1, C1 |       | 0  | 1, C1 |

-continued

|    | R1 | R2 | R3    | D1 | C1    | D2    | C2    |
|----|----|----|-------|----|-------|-------|-------|
| D2 | 0  | 0  | 0     | 0  | 0     |       | 1, D2 |
| C2 | 0  | 0  | 1, C2 | 0  | 1, C2 | 1, C2 |       |

There are no changes, showing that R3 does not make a good middle-point.

D1 Middle Point

| Start  | R1                                          | R1                                           | R1                                           | R1                                            | R1                                           | R1                                           | R1                                           |
|--------|---------------------------------------------|----------------------------------------------|----------------------------------------------|-----------------------------------------------|----------------------------------------------|----------------------------------------------|----------------------------------------------|
| Middle | D1                                          | D1                                           | D1                                           | D1                                            | D1                                           | D1                                           | D1                                           |
| End    | R1                                          | R2                                           | R3                                           | D1                                            | C1                                           | D2                                           | C2                                           |
| Result | Invalid - start cannot be equal to end      | 0                                            | 0                                            | Invalid - middle cannot be equal to end       | 0                                            | 0                                            | 0                                            |
| Start  | R2                                          | R2                                           | R2                                           | R2                                            | R2                                           | R2                                           | R2                                           |
| Middle | D1                                          | D1                                           | D1                                           | D1                                            | D1                                           | D1                                           | D1                                           |
| End    | R1                                          | R2                                           | R3                                           | D1                                            | C1                                           | D2                                           | C2                                           |
| Result | 0                                           | Invalid - start cannot be equal to end       | 0                                            | Invalid - middle cannot be equal to end       | 0                                            | 0                                            | 0                                            |
| Start  | R3                                          | R3                                           | R3                                           | R3                                            | R3                                           | R3                                           | R3                                           |
| Middle | D1                                          | D1                                           | D1                                           | D1                                            | D1                                           | D1                                           | D1                                           |
| End    | R1                                          | R2                                           | R3                                           | D1                                            | C1                                           | D2                                           | C2                                           |
| Result | 0                                           | 0                                            | Invalid - start cannot be equal to end       | Invalid - middle cannot be equal to end       | 0                                            | 0                                            | 0                                            |
| Start  | D1                                          | D1                                           | D1                                           | D1                                            | D1                                           | D1                                           | D1                                           |
| Middle | D1                                          | D1                                           | D1                                           | D1                                            | D1                                           | D1                                           | D1                                           |
| End    | R1                                          | R2                                           | R3                                           | D1                                            | C1                                           | D2                                           | C2                                           |
| Result | Invalid - start cannot be equal to middle   | Invalid - start cannot be equal to middle    | Invalid - start cannot be equal to middle    | Invalid - start cannot be equal to middle     | Invalid - start cannot be equal to middle    | Invalid - start cannot be equal to middle    | Invalid - start cannot be equal to middle    |
| Start  | C1                                          | C1                                           | C1                                           | C1                                            | C1                                           | C1                                           | C1                                           |
| Middle | D1                                          | D1                                           | D1                                           | D1                                            | D1                                           | D1                                           | D1                                           |
| End    | R1                                          | R2                                           | R3                                           | D1                                            | C1                                           | D2                                           | C2                                           |
| Result | 0                                           | 0                                            | 0                                            | Invalid - middle cannot be equal to end       | Invalid - start cannot be equal to end       | 0                                            | 0                                            |
| Start  | D2                                          | D2                                           | D2                                           | D2                                            | D2                                           | D2                                           | D2                                           |
| Middle | D1                                          | D1                                           | D1                                           | D1                                            | D1                                           | D1                                           | D1                                           |
| End    | R1                                          | R2                                           | R3                                           | D1                                            | C1                                           | D2                                           | C2                                           |
| Result | 0                                           | 0                                            | 0                                            | Invalid - middle cannot be equal to end       | 0                                            | Invalid - start cannot be equal to end       | 0                                            |
| Start  | C2                                          | C2                                           | C2                                           | C2                                            | C2                                           | C2                                           | C2                                           |
| Middle | D1                                          | D1                                           | D1                                           | D1                                            | D1                                           | D1                                           | D1                                           |
| End    | R1                                          | R2                                           | R3                                           | D1                                            | C1                                           | D2                                           | C2                                           |
| Result | 0                                           | 0                                            | 0                                            | Invalid - middle cannot be equal to end       | 0                                            | 0                                            | Invalid - start cannot be equal to end       |

At the end of this stage, the most efficient matrix looks like this:

|    | R1    | R2    | R3 | D1    | C1    | D2 | C2    |
|----|-------|-------|----|-------|-------|----|-------|
| R1 |       | 0     | 0  | 0     | 1, R1 | 0  | 0     |
| R2 | 0     |       | 0  | 0     | 1, R2 | 0  | 0     |
| R3 | 0     | 0     |    | 0     | 0     | 0  | 1, R3 |
| D1 | 0     | 0     | 0  |       | 1, D1 | 0  | 0     |
| C1 | 1, C1 | 1, C1 | 0  | 1, C1 |       | 0  | 1, C1 |
| D2 | 0     | 0     | 0  | 0     | 0     |    | 1, D2 |
| C2 | 0     | 0     | 1, C2 | 0  | 1, C2 | 1, C2 |   |

There are no changes, showing that R3 does not make a good middle-point.

C1 Middle Point

| Start | R1 | R1 | R1 | R1 | R1 | R1 | R1 |
|---|---|---|---|---|---|---|---|
| Middle | C1 | C1 | C1 | C1 | C1 | C1 | C1 |
| End | R1 | R2 | R3 | D1 | C1 | D2 | C2 |
| Result | Invalid - start cannot be equal to end | 2, C1 | 0 | 2, C1 | Invalid - middle cannot be equal to end | 0 | 2, C1 |
| Start | R2 | R2 | R2 | R2 | R2 | R2 | R2 |
| Middle | C1 | C1 | C1 | C1 | C1 | C1 | C1 |
| End | R1 | R2 | R3 | D1 | C1 | D2 | C2 |
| Result | 2, C1 | Invalid - start cannot be equal to end | 0 | 2, C1 | Invalid - middle cannot be equal to end | 0 | 2, C1 |
| Start | R3 | R3 | R3 | R3 | R3 | R3 | R3 |
| Middle | C1 | C1 | C1 | C1 | C1 | C1 | C1 |
| End | R1 | R2 | R3 | D1 | C1 | D2 | C2 |
| Result | 0 | 0 | Invalid - start cannot be equal to end | 0 | Invalid - middle cannot be equal to end | 0 | 0 |
| Start | D1 | D1 | D1 | D1 | D1 | D1 | D1 |
| Middle | C1 | C1 | C1 | C1 | C1 | C1 | C1 |
| End | R1 | R2 | R3 | D1 | C1 | D2 | C2 |
| Result | 2, C1 | 2, C1 | 0 | Invalid - start cannot be equal to end | Invalid- start cannot be equal to middle | 0 | 2, C1 |
| Start | C1 | C1 | C1 | C1 | C1 | C1 | C1 |
| Middle | C1 | C1 | C1 | C1 | C1 | C1 | C1 |
| End | R1 | R2 | R3 | D1 | C1 | D2 | C2 |
| Result | Invalid - start cannot be equal to middle | Invalid - start cannot be equal to middle | Invalid - start cannot be equal to middle | Invalid - start cannot be equal to middle | Invalid - start cannot be equal to middle | Invalid - start cannot be equal to middle | Invalid - start cannot be equal to middle |
| Start | D2 | D2 | D2 | D2 | D2 | D2 | D2 |
| Middle | C1 | C1 | C1 | C1 | C1 | C1 | C1 |
| End | R1 | R2 | R3 | D1 | C1 | D2 | C2 |
| Result | 0 | 0 | 0 | 0 | Invalid - middle cannot be equal to end | Invalid - start cannot be equal to end | 0 |
| Start | C2 | C2 | C2 | C2 | C2 | C2 | C2 |
| Middle | C1 | C1 | C1 | C1 | C1 | C1 | C1 |
| End | R1 | R2 | R3 | D1 | C1 | D2 | C2 |
| Result | 2, C1 | 2, C2 | 0 | 2, C1 | Invalid - middle cannot be equal to end | 0 | Invalid - start cannot be equal to end |

At the end of this stage, the most efficient matrix looks like this:

|    | R1    | R2    | R3 | D1    | C1    | D2 | C2    |
|----|-------|-------|----|-------|-------|----|-------|
| R1 |       | 2, C1 | 0  | 2, C1 | 1, R1 | 0  | 2, C1 |
| R2 | 2, C1 |       | 0  | 2, C1 | 1, R2 | 0  | 2, C1 |
| R3 | 0     | 0     |    | 0     | 0     | 0  | 1, R3 |
| D1 | 2, C1 | 2, C1 | 0  |       | 1, D1 | 0  | 2, C1 |
| C1 | 1, C1 | 1, C1 | 0  | 1, C1 |       | 0  | 1, C1 |

-continued

|    | R1    | R2    | R3    | D1    | C1    | D2    | C2    |
|----|-------|-------|-------|-------|-------|-------|-------|
| D2 | 0     | 0     | 0     | 0     | 0     |       | 1, D2 |
| C2 | 2, C1 | 2, C1 | 1, C2 | 2, C1 | 1, C2 | 1, C2 |       |

The items added as a result of this pass (testing C1 as middle) are in underlined text. These results indicate that C1 is a good middle point.

D2 Middle Point

| Start | R1 | R1 | R1 | R1 | R1 | R1 | R1 |
|-------|----|----|----|----|----|----|----|
| Middle | D2 | D2 | D2 | D2 | D2 | D2 | D2 |
| End | R1 | R2 | R3 | D1 | C1 | D2 | C2 |
| Result | Invalid - start cannot be equal to end | 0 | 0 | 0 | 0 | Invalid - middle cannot be equal to end | 0 |
| Start | R2 | R2 | R2 | R2 | R2 | R2 | R2 |
| Middle | D2 | D2 | D2 | D2 | D2 | D2 | D2 |
| End | R1 | R2 | R3 | D1 | C1 | D2 | C2 |
| Result | 0 | Invalid - start cannot be equal to end | 0 | 0 | 0 | Invalid - middle cannot be equal to end | 0 |
| Start | R3 | R3 | R3 | R3 | R3 | R3 | R3 |
| Middle | D2 | D2 | D2 | D2 | D2 | D2 | D2 |
| End | R1 | R2 | R3 | D1 | C1 | D2 | C2 |
| Result | 0 | 0 | Invalid - start cannot be equal to end | 0 | 0 | Invalid - middle cannot be equal to end | 0 |
| Start | D1 | D1 | D1 | D1 | D1 | D1 | D1 |
| Middle | D2 | D2 | D2 | D2 | D2 | D2 | D2 |
| End | R1 | R2 | R3 | D1 | C1 | D2 | C2 |
| Result | 0 | 0 | 0 | Invalid - start cannot be equal to end | 0 | Invalid - middle cannot be equal to end | 0 |
| Start | C1 | C1 | C1 | C1 | C1 | C1 | C1 |
| Middle | D2 | D2 | D2 | D2 | D2 | D2 | D2 |
| End | R1 | R2 | R3 | D1 | C1 | D2 | C2 |
| Result | 0 | 0 | 0 | 0 | Invalid - start cannot be equal to end | Invalid - middle cannot be equal to end | 0 |
| Start | R1 | R2 | R3 | D1 | C1 | D2 | C2 |
| Middle | D2 | D2 | D2 | D2 | D2 | D2 | D2 |
| End | D2 | D2 | D2 | D2 | D2 | D2 | D2 |
| Result | Invalid - middle cannot be equal to end | Invalid - middle cannot be equal to end | Invalid - middle cannot be equal to end | Invalid - middle cannot be equal to end | Invalid - middle cannot be equal to end | Invalid - middle cannot be equal to end | Invalid - middle cannot be equal to end |
| Start | C2 | C2 | C2 | C2 | C2 | C2 | C2 |
| Middle | D2 | D2 | D2 | D2 | D2 | D2 | D2 |
| End | R1 | R2 | R3 | D1 | C1 | D2 | C2 |
| Result | 0 | 0 | 0 | 0 | 0 | Invalid - middle cannot be equal to end | Invalid - start cannot be equal to end |

At the end of this stage, the leas-cost matrix looks like this:

|    | R1   | R2   | R3 | D1   | C1   | D2   | C2   |
|----|------|------|----|------|------|------|------|
| R1 |      | 2, C1| 0  | 2, C1| 1, R1| 0    | 2, C1|
| R2 | 2, C1|      | 0  | 2, C1| 1, R2| 0    | 2, C1|
| R3 | 0    | 0    |    | 0    | 0    | 0    | 1, R3|
| D1 | 2, C1| 2, C1| 0  |      | 1, D1| 0    | 2, C1|
| C1 | 1, C1| 1, C1| 0  | 1, C1|      | 0    | 1, C1|

-continued

|    | R1   | R2   | R3   | D1   | C1   | D2   | C2   |
|----|------|------|------|------|------|------|------|
| D2 | 0    | 0    | 0    | 0    | 0    |      | 1, D2|
| C2 | 2, C1| 2, C1| 1, C2| 2, C1| 1, C2| 1, C2|      |

There are no changes, showing that D2 is not a good middle point.

C2 Middle Point

| Start | R1 | R1 | R1 | R1 | R1 | R1 | R1 |
|---|---|---|---|---|---|---|---|
| Middle | C2 | C2 | C2 | C2 | C2 | C2 | C2 |
| End | R1 | R2 | R3 | D1 | C1 | D2 | C2 |
| Result | Invalid - Start cannot be equal to end | 4, C1 Discard because this is greater than 2, C1 | 3, C2 | 4, C1 Discard because this is greater than 2, C1 | 3, C2 Discard because this is greater than 1, R1 | 3, C2 | Invalid - middle cannot be equal to end |
| Start | R2 | R2 | R2 | R2 | R2 | R2 | R2 |
| Middle | C2 | C2 | C2 | C2 | C2 | C2 | C2 |
| End | R1 | R2 | R3 | D1 | C1 | D2 | C2 |
| Result | 4, C1 Discard because this is greater than 2, C1 | Invalid - start cannot be equal to end | 3, C2 | 4, C1 Discard because this is greater than 2, C1 | 3, C2 Discard because this is greater than 1, R2 | 3, C2 | Invalid - middle cannot be equal to end |
| Start | R3 | R3 | R3 | R3 | R3 | R3 | R3 |
| Middle | C2 | C2 | C2 | C2 | C2 | C2 | C2 |
| End | R1 | R2 | R3 | D1 | C1 | D2 | C2 |
| Result | 3, C1 | 3, C1 | Invalid - start cannot be equal to end | 3, C1 | 2, C2 | 2, C2 | Invalid - middle cannot be equal to end |
| Start | D1 | D1 | D1 | D1 | D1 | D1 | D1 |
| Middle | C2 | C2 | C2 | C2 | C2 | C2 | C2 |
| End | R1 | R2 | R3 | D1 | C1 | D2 | C2 |
| Result | 4, C1 Discard because this is greater than 2, C1 | 4, C1 Discard because this is greater than 2, C1 | 3, C2 | Invalid - start cannot be equal to end | 4, C2 Discard because this is greater than 1, D1 | 3, C2 | Invalid - middle cannot be equal to end |
| Start | C1 | C1 | C1 | C1 | C1 | C1 | C1 |
| Middle | C2 | C2 | C2 | C2 | C2 | C2 | C2 |
| End | R1 | R2 | R3 | D1 | C1 | D2 | C2 |
| Result | 3, C1 Discard because this is greater than 2, C1 | 3, C1 Discard because this is greater than 2, C1 | 2, C2 | 3, C1 Discard because this is greater than 1, C1 | Invalid - start cannot be equal to end | 2, C2 | Invalid - middle cannot be equal to end |
| Start | D2 | D2 | D2 | D2 | D2 | D2 | D2 |
| Middle | C2 | C2 | C2 | C2 | C2 | C2 | C2 |
| End | R1 | R2 | R3 | D1 | C1 | D2 | C2 |
| Result | 3, C1 | 3, C1 | 2, C2 | 3, C1 | 2, C2 | Invalid - start cannot be equal to end | Invalid - middle cannot be equal to end |
| Start | R1 | R2 | R3 | D1 | C1 | D2 | C2 |
| Middle | C2 | C2 | C2 | C2 | C2 | C2 | C2 |
| End | C2 | C2 | C2 | C2 | C2 | C2 | C2 |
| Result | Invalid - middle cannot be equal to end | Invalid - middle cannot be equal to end | Invalid - middle cannot be equal to end | Invalid - middle cannot be equal to end | Invalid - middle cannot be equal to end | Invalid - middle cannot be equal to end | Invalid - middle cannot be equal to end |

At the end of this stage, the most efficient matrix looks like this:

|    | R1    | R2    | R3    | D1    | C1    | D2    | C2    |
|----|-------|-------|-------|-------|-------|-------|-------|
| R1 |       | 2, C1 | 3, C2 | 2, C1 | 1, R1 | 3, C2 | 2, C1 |
| R2 | 2, C1 |       | 3, C2 | 2, C1 | 1, R2 | 3, C2 | 2, C1 |
| R3 | 3, C1 | 3, C1 |       | 3, C1 | 2, C2 | 2, C2 | 1, R3 |
| D1 | 2, C1 | 2, C1 | 3, C2 |       | 1, D1 | 3, C1 | 2, C1 |
| C1 | 1, C1 | 1, C1 | 2, C2 | 1, C1 |       | 2, C2 | 1, C1 |
| D2 | 3, C1 | 3, C1 | 2, C2 | 3, C1 | 2, C2 |       | 1, D2 |
| C2 | 2, C1 | 2, C1 | 1, C2 | 2, C1 | 1, C2 | 1, C2 |       |

The items added as a result of this pass (testing C2 as middle) are in underlined text. These results indicate that C2 is a good middle point. The matrix now contains the most efficient route between each pair of points in the network.

EXAMPLE 2

Least Cost Routing in a Multi-zone Network

Example 2 describes an application for an Automated Scheduling System (VC Wizard) to manage least cost routing and automated device control in a multi-zone, multi-campus network (shown in FIG. 4) that uses H.323 IP Cisco 3511 and 3540 MCUs for multi-point conferencing. This multi-zone, multi-campus network is linked by three wide area network (WAN) links, each with different H.323 zone call prefixes and WAN costs.

Figure 4:
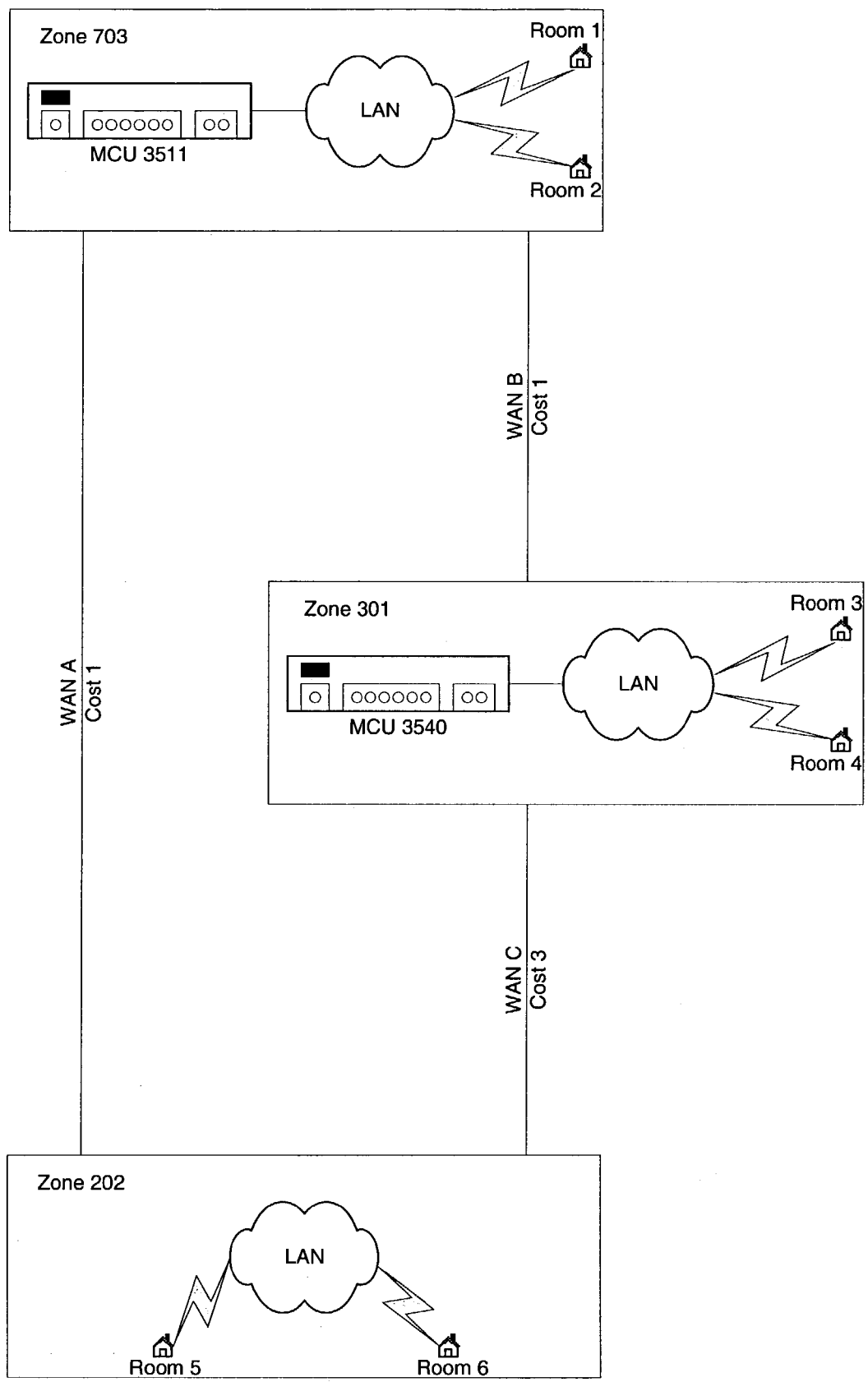
FIG. 4 is a diagram depicting a multi-zone network model.

In the network shown in FIG. 4, calls are bridged on the local area network (LAN) except when inter-zone calls are required. For inter-zone calls, the Automated Scheduling System must:

- use least cost routing to connect calls across the least expensive WAN link
- add the correct dialing prefixes for inter-zone calls automatically
- bridge all connections automatically using automated device control Based on the network in FIG. 4, assume a videoconference must include Rooms 1, 3, 4, and 6. The software applies the least cost routing algorithm as follows.

Least Cost Routing for Multi-Zone Conferences

After completing steps 1–3, the software builds the device array, which includes the MCUs from Zone 703 and Zone 301. At steps 5 and 6, the program generates an adjacency matrix and determines the list of possible routes. Based on the least expensive route, the software nominates a hosting device. In this case, based on the number of endpoints in Zone 301, the software selects MCU 3540 to host the call.

At step 8 and 9, the software determines the actual routes from each endpoint to the host device. Rooms 3 and 4, which are in the same zone as MCU 3540, are routed locally via the LAN. The software routes Room 1, in Zone 703, through WAN B.

When determining the route to connect Room 6 to the host device, the software must compare the cost of two possible routes, as shown in Table 12.

TABLE 12

Cost of connecting to host device.

|       | Cost of Connection | |
|-------|-------------|------------------|
|       | Via Zone 703 | Direct Connection |
| WAN A | 1           | Not used          |
| WAN B | 1           | Not used          |
| WAN C | Not used    | 3                 |
| Total Cost | 2      | 3                 |

Based on the cost of connection, the software connects Room 6 to the host device by way of WANs A and B. This route is less expensive due to the higher cost of using WAN C.

Multi-Zone Networks and Cascaded Conferences

Cascading a conference allows more participants to be included in a single conference. In a cascaded conference, two or more MCUs are connected through WAN links. Some endpoints are hosted on one local MCU and others on a different local MCU. In this circumstance, the cost to bridge the conference locally is less than using the WAN link.

For example, assume the videoconference requires Rooms 1, 2, 3, and 4. In this case, the cost of using WAN links recommends against using either MCU as the conference host. Instead, the least cost route connects each room to the MCU in its local zone. Then, the software cascades the MCUs together, using the WAN link only once, to bridge the conference.

Automated Device Control

Once the device and endpoint information has been set up properly, the automated schedule and control system is capable of automatically starting all the devices in the conference. In all cases, conference status, failures, and error messages may be displayed and recorded for analysis.

The schedule and control system can automate and manage the MCUs and endpoints using telnet, SNMP, and XML commands. These commands allow the automated schedule and control system to:

- download all services previously created in the MCU automatically
- invite endpoints to conferences automatically
- set Continuous Presence Layout positions
- provide cascading capabilities
- allocate resources with the proper service hunting
- generate call prefixes At conference start time, the automated schedule and control system logs on to the MCU. Through the Device Control System (DCS), the software sends special SNMP commands to create a conference shell specific to the service parameters previously selected by the system for this conference. These parameters detail information about the conference such as number of participants, speed, type of conference, etc.

The conference shell can be protected from unwarranted access by requiring a pass code on the MCU, such as a Service ID and/or Conference ID. After creating the conference shell, the automated schedule and control system automatically invites all rooms designated as Dial-out to the conference using special SNMP commands, including the correct zone prefix order and dial plan numbers. The Dial-out endpoint connections are routed to the MCU with the help of the H.323 Gatekeeper. Rooms designated as Dial-in must dial the conference using the correct zone prefix order and pass code to gain access.

Persons of ordinary skill in the art will recognize that many modifications may be made to the present invention without departing from its spirit and scope. The embodiments described herein are meant to be illustrative only and should not be taken as limiting the invention, which is defined by the following claims.

The invention claimed is:

1. A method for connecting a videoconference through a telecommunication system including multiple telecommunication devices and endpoint stations operatively connected via route segments comprising the steps of:
   a) providing a database in a telecommunication host facility including a network model of the telecommunication system;
   b) entering endpoint station indicia, telecommunications device operating indicia and route segment indicia at the host facility database;
   c) establishing an adjacency matrix having matrix nodes based on endpoint stations and telecommunication devices;
   d) assigning efficiency value to each route segment in the matrix;
   e) calculating the most efficient routing for the videoconference by employing a Floyd-type graph algorithm;
   f) verifying compatability of the network model of the telecommunication system;
   g) nominating a primary bridging device from a plurality of bridging devices for interconnecting the telecommunication devices and endpoint stations as a function of steps e) and f) above;
   h) recording verified routing in the host facility database; and controlling devices and endpoints automatically.

2. A method for connecting a videoconference through a telecommunication system according to claim 1 wherein the telecommunication network includes an Internet network, and wherein at least a portion of the route segments are assigned differing cost efficiency values.

3. A method for connecting a videoconference through a telecommunication system comprising videoconferencing rooms and telecommunication devices operatively connected through route segments, comprising the steps of:
   A) representing the telecommunication devices and videoconferencing rooms as network nodes in a computer-stored adjacency matrix,
   B) applying a computer graph algorithm for determining least cost routing, whereby the least cost routing is allocated in advance for an entire proposed conference event;
   C) employing a resource counting algorithm to determine if the device's capacity allows the proposed conference event to be scheduled the steps of:
   i) determining a first conference resource that overlaps the proposed conference event time,
   ii) creating a new time period that as an intersection of the overlapping conference resource time and the proposed conference event time,
   iii) generating a new list of conference resources by including remaining resources in use at anytime in the intersection time period, said new list indicating a potential number of resources in use at the same time as the first resource in the original list,
   iv) sequentially moving to each of the other resources in the list generating new time periods and new lists, tracking the number of other resources simultaneously in use, and saving the maximum number of recursive calls as a solution
   v) if the number of remaining resources in a list is less than the current maximum number of recursive calls, as determined in step iv), stopping processing the current list and returning to a previous list of resources,
   vi) checking the current list size against the current maximum count speeds up the calculation by omitting needless computation, and
   vii) confirming that the maximum count of resources in simultaneous use is less than the device's capacity limits.

* * * * *